United States Patent [19]

Albarda

[11] Patent Number: 4,587,966
[45] Date of Patent: May 13, 1986

[54] DEVICE FOR EVALUATING THE MIXING OF LIQUID ANESTHETIC AND A RESPIRATORY GAS FOR PATIENTS

[75] Inventor: Scato Albarda, Gross Schenkenberg, Fed. Rep. of Germany

[73] Assignee: Drägerwerk Aktiengesellschaft, Fed. Rep. of Germany

[21] Appl. No.: 531,689

[22] Filed: Sep. 13, 1983

[30] Foreign Application Priority Data

Sep. 17, 1982 [DE] Fed. Rep. of Germany ....... 3234474

[51] Int. Cl.$^4$ .............................................. A61M 16/00
[52] U.S. Cl. .......................... 128/202.22; 128/203.17; 128/204.17; 219/272; 219/273; 219/276; 261/130; 261/DIG. 65
[58] Field of Search ....................... 128/200.11, 203.12, 128/203.14, 203.17, 203.25, 203.26, 203.27, 204.14, 204.17, 204.21, 204.22, 200.14, 200.21, 202.22; 219/323, 324, 325, 327, 328, 330, 378, 379, 491, 286, 272, 273, 276; 261/129, 130, 131, 133

[56] References Cited

U.S. PATENT DOCUMENTS

| 4,201,204 | 5/1980 | Rinne et al. | 128/203.27 |
| 4,401,114 | 8/1983 | Lwoff et al. | 128/204.17 |
| 4,477,395 | 10/1984 | Albarda | 128/203.27 |
| 4,484,576 | 11/1984 | Albarda | 261/DIG. 65 |

FOREIGN PATENT DOCUMENTS 195028 5/1957 Austria ..................... 128/203.27

Primary Examiner—Henry J. Recla
Assistant Examiner—Karin M. Reichle
Attorney, Agent, or Firm—McGlew and Tuttle

[57] ABSTRACT

A device for admixing liquid anesthetics into the respiratory gas to be supplied to a patient makes it possible to monitor the concentration, the flow of respiratory gas, the mixture ratio, and the flow of anesthetic. Errors may thus be indicated and safety is increased in medical practice. The device utilizes the phenomonen that during the evaporation of an anesthetic admixed with the respiratory gas, the temperature in the thermally insulated ambience of the mixing chamber drops by an amount depending on the ratio of the vaporized anesthetic to the respiratory gas, thus on the concentration. The temperatures are measured at the inlet of the mixing chamber by an inlet sensor and an intermediate sensor, and at the outlet of the mixing chamber by an outlet sensor. Upon heating the stream of respiratory gas by means of a heating element in the inlet portion, the breathing gas flow, its mixing ratio, and the flow of anesthetic can be measured, and thus the concentration can be determined from the necessary heating power input and the heating temperature. The measurement is effected by a heater control and evaluating circuit connected to the sensors and the heater, by which heater controlling measures are effected upon deviations from desired values.

2 Claims, 2 Drawing Figures

DEVICE FOR EVALUATING THE MIXING OF LIQUID ANESTHETIC AND A RESPIRATORY GAS FOR PATIENTS

FIELD AND BACKGROUND OF THE INVENTION

This invention relates in general to respiratory devices and in particular to a new and useful evaluating device for liquid anesthetic and respiratory gas mixtures for patients.

In medical apparatus, where any malfunction may endanger the patient, it is a matter of course that the function of all parts and their assemblies is monitored by other, independently operating parts, or that interconnections are provided delivering signals as soon as differences between desired and actual values appear. Such signals release visual or acoustic alarms and/or automatic remedial measures, such as switching to standby assemblies.

A prior art apparatus for admixing liquid anesthetics to the breathing gas to be supplied to a patient is designed for monitoring the concentration, the breathing gas flow, and the amount of liquid anesthetic. The phenomenon is utilized that during the evaporation of a liquid anesthetic admixed to the respiratory gas, a temperature drop is observed which depends on the ratio between the amount of evaporated anesthetic and the amount of respiratory gas. Through an inlet, the respiratory gas along with the anesthetic are introduced from the outside into a thermally insulated mixing chamber. The supply conduit opens into the mixing chamber tangentially to form a cyclonic or whirling flow. Upstream of the mixing chamber, the supply conduit forms within the inlet a heat exchanger. Between the heat exchanger and the mixing chamber, an inlet temperature sensor extends into the inlet. An outlet for the mixture of respiratory gas and evaporated anesthetic connects to the outside, to the patient. Downstream of the mixing chamber, an outlet temperature sensor is provided. The wall of the mixing chamber is equipped with an electrical heating element. The two measuring sensors and the heating element are connected to a control and evaluating circuit which periodically switches between two operating phases. During the first phase, the heating is controlled to maintain equality between the temperature measurements of the two sensors. The supplied heating power thus corresponds to the heat of evaporation of the supplied amount of anesthetic, and is a measure of the flow of anesthetic. During the second phase, the heating is switched off and upon a complete evaporation, the temperature difference established between the two temperature sensors is determined. This difference depends on the ratio of the evaporative amount of anesthetic to the amount of respiratory gas, and thus is a measure of the concentration of the anesthetic in the respiratory gas. The quotient of the results of measurement in the two phases is a measure of the rate of flow of respiratory gas, i.e.

(flow of anesthetic)/(concentration of anesthetic)=flow of respiratory gas (German Pat. No. 31 16 951, U.S. Pat. No. 4,477,395).

SUMMARY OF THE INVENTION

The present invention is directed to an evaluating device for liquid anesthetic and respiratory gas mixture which is simple in construction and provides a continuous check on the set values of the concentration of the anaesthetic vapour and of the composition of the gas mixture even to extreme requirements on breathing gas amounts, and makes possible secure monitoring by operators.

A device for evaluating the admixing liquid anesthetics and the respiratory gas to be supplied to a patient comprises a heater control and evaluating circuit. The apparatus includes a thermally insulated housing having a mixing chamber with an inlet portion for the respiratory gas and an outlet portion for a mixture of the respiratory gas which is mixed with the evaporated anesthetic. The housing also has an inlet portion for the respiratory gas and an outlet portion for a mixture of the respiratory gas mixed with the evaporated anesthetic. Inlet and outlet temperature sensors are provided in the inlet and outlet portions. A heating element is located in the inlet portion and an intermediate temperature sensor located downstream of the heater. The inlet temperature sensor is located adjacent the entrance of the inlet conduit. An anesthetic line for supplying the anesthetic enters into the housing and has a heat exchanger portion located in the entrance area of the inlet portion upstream of the inlet temperature sensor. The anesthetic line extends through the housing and bypasses the heating element portion of the inlet and opens up again into the inlet portion downstream of the intermediate temperature sensor and terminates with the inlet portion in the mixing chamber.

The input power of the heating element is measured through an ammeter and a voltmeter and determined by a wattmeter. The wattmeter output also corresponds to anesthetic flow and this is indicated by an indicator. The wattmeter signal is also simultaneously applied to a computer. Also simultaneously applied to the computer are the values measured by the ammeter and voltmeter through an ohmmeter as the signal thereof. The construction includes a differential amplifier connected to the inlet and intermediate temperature sensors which measures the difference between the temperature measured by the inlet temperature sensor and the intermediate temperature sensor resulting from the heating of the respiratory gas by means of the heating element in the inlet portion.

The computer is connected to a respiratory gas flow indicator and to a concentration indicator or to an indicator of the mixing ratio of the respiratory gas.

The inventive device makes it possible to monitor the flow of the anesthetic, the flow of the respiratory gas, the mixing ratio, and the concentration. The provision of a third temperature sensor, the intermediate one, between the inlet temperature sensor and the outlet temperature sensor, but still within the inlet portion, downstream of the heating element, ensures that the monitoring of the anesthetic and the respiratory gas flow, mixing ratio, and concentration can be effected continuously. Due to the heating provided in the inlet portion, the liquid anesthetic can be evaporated completely.

The basis for determining the monitored values are measuring of the power supply to and temperature of the heating element by determining the voltage and amperage, and the known data of the three temperature sensors, of the anesthetic, and of the respiratory gas components.

Since the measurements take place simultaneously, all measured values are available at any time, provided that the thermal time constant of the device is taken into account.

Accordingly, it is an object of the invention to provide an evaluating device for admixing of a liquid anesthetic with a respiratory gas mixtures which comprises a housing having a mixing chamber with an inlet conduit extending into the housing for supplying respiratory gas and into the mixing chamber including an outlet for the admixed gas anesthetic and further including an inlet for the anesthetic which has a heat exchanger portion located in the inlet conduit for the respiratory gas which is discharged into the mixing chamber along with the respiratory gas after the respiratory gas has passed a heater and including electrical heater control means connected to each of three separate indicators located adjacent the entrance to the anesthetic inlet, intermediate the length of the anesthetic inlet and at the location of the outlet conduit for regulating the heater.

A further object of the invention is to provide such a device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
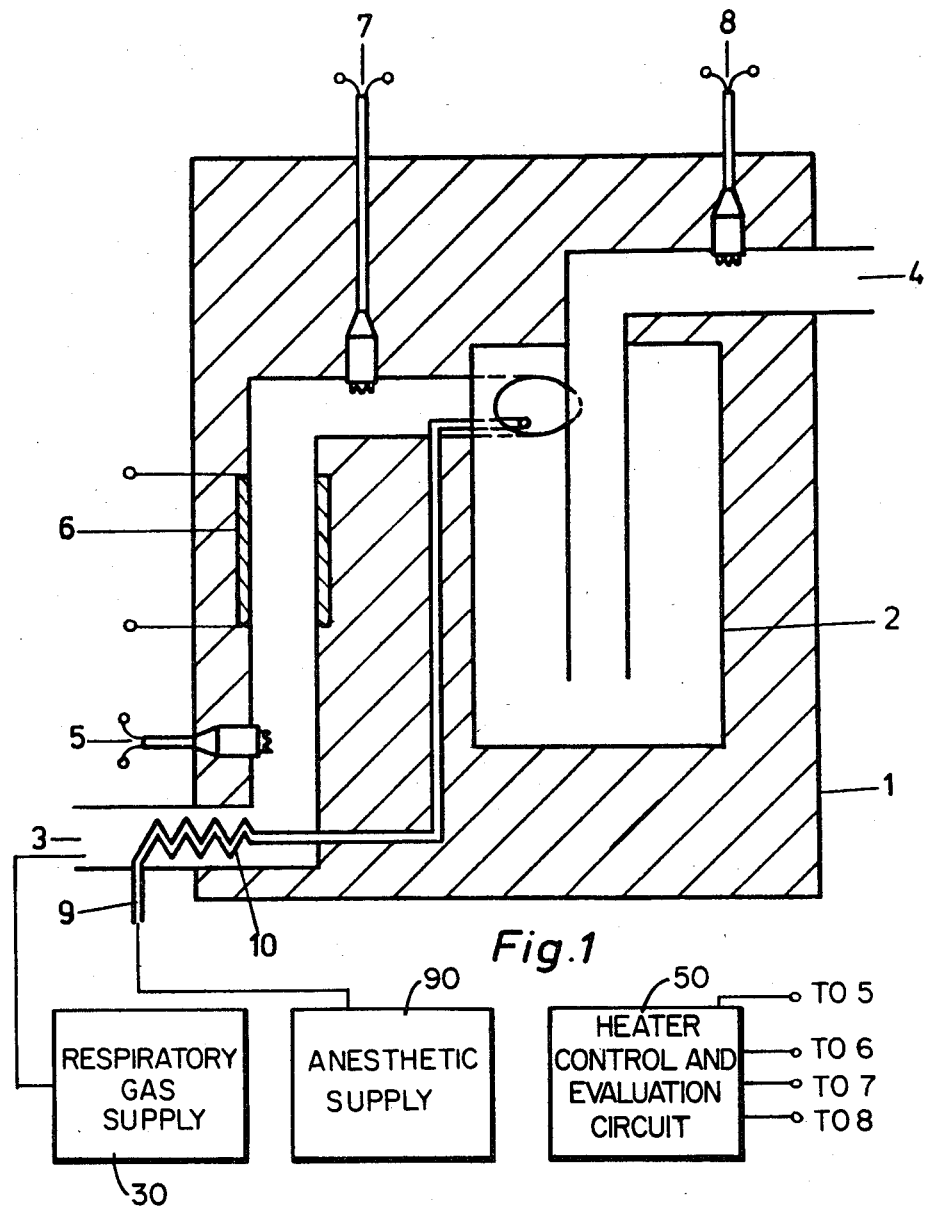
FIG. 1 is a schematic sectional view of a device for evaluating liquid anesthetics and repiratory gas mixtures constructed in accordance with the invention.

Referring to the drawings in particular the invention embodied therein comprises an evaluating device for a liquid anesthetic from an anesthetic supply 90 with a respiratory gas from a respiratory gas supply 30. The device includes a housing 1 having a mixing chamber 2 therein. The respiratory gas supply 30 is connected to an inlet conduit 3 which extends into the housing 1 and terminates in the mixing chamber 2. Anesthetic supply 90 comprises a liquid anesthetic which is fed through an anesthetic liquid inlet portion or conduit 9 which has a heat exchanger part 10 located at the entrance of the respiratory gas inlet conduit into the housing 1. The anesthetic gas supply conduit 9 extends from the heat exchanger portion 10 through the housing and bypasses the portion of the inlet conduit 3 which contains a heater 6 and discharges into the mixing chamber 2. The heater 6 is located in the housing to heat respiratory gas downstream of the heat exchanger 10. The temperature sensor 5 is located between the heat exchanger 10 and the heater 6. A further temperature sensor 7 is located between the heater 6 and the discharge of the conduit 3 into the mixing chamber 2.

An outlet conduit 4 extends from the mixing chamber 2 through the housing 1 to the exterior thereof. A temperature sensor 8 is located in the outlet conduit between the mixing chamber and the exterior of the housing. Electrical heater control means 50 are connected to each of the temperature sensors 5, 7 and 8 and to the heater 6 in such a way that the temperature T5 and T8 are kept equal.

A thermally insulated housing 1 accommodates a mixing chamber 2 which is provided with an inlet conduit or portion 3 and an outlet conduit portion 4. Within the inlet portion 3, there is an inlet temperature sensor 5, an electrical heating element 6, and, downstream thereof, an intermediate temperature sensor 7. In the outlet portion 4, thus downstream of mixing chamber 2, an outlet temperature sensor 8 is mounted. At a location within inlet portion 3, upstream of inlet temperature sensor 5, a line 9 for supplying a liquid anesthetic is formed with a coil portion 10 serving as a heat exchanger. Therefrom, line 9 extends through housing 1 along a path different from inlet portion 3. It rejoins inlet portion 3 downstream of intermediate temperature sensor 7 and opens along therewith tangentially into the mixing chamber 2.

The respiratory gas is supplied through inlet portion 3, wherefrom it flows tangentially into mixing chamber 2. In the cyclonic pool there forming the liquid anesthetic introduced through line 9 evaporates and mixes uniformly with the respiratory gas. Due to the equalizing effect of the heat exchanger 10, the respiratory gas and the liquid anesthetic after the heat exchanger have the same temperature. The temperature is measured through inlet temperature sensor 5. Heating element 6 raises the temperature of the respiratory gas upstream of mixing chamber 2 to an intermediate temperature which is measured by means of intermediate temperature sensor 7. Outlet temperature sensor 8 measures the temperature of the mixture of respiratory gas and anesthetic leaving mixing chamber 2 through outlet 4.

Figure 2:
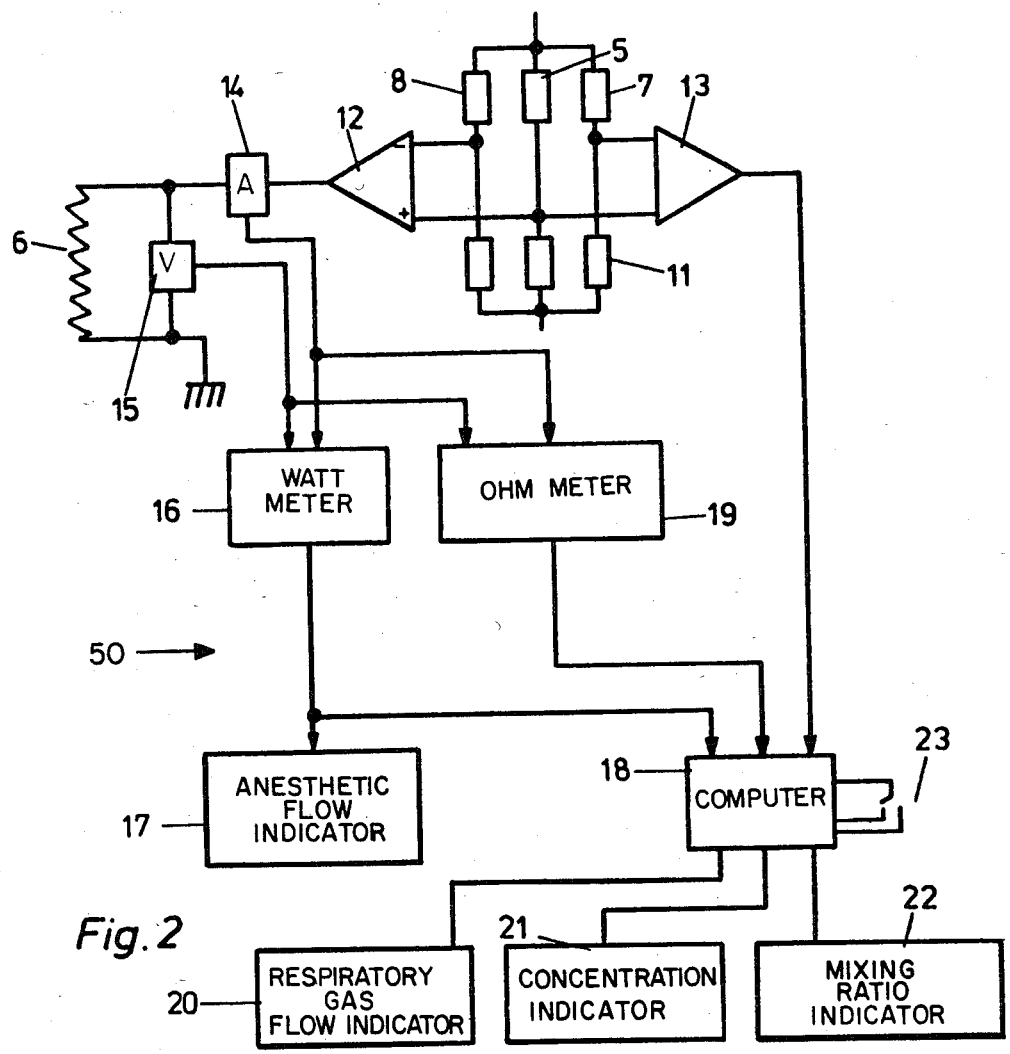
FIG. 2 is a schematic diagram of the heater control and evaluating circuit for the device shown in FIG. 1.

The heater control and evaluating circuit schematically shown in FIG. 2 controls the above device, with (a) the rate of flow $M_g$ of the respiratory gas and (b) the rate of flow $M_N$ of the anesthetic being predetermined, (c) the temperature $T_5$ at inlet temperature sensor 5 and $T_8$ and outlet temperature sensor 8 being equal to each other, $T_5 = T_8$, (d) the temperature $T_7$ at intermediate temperature sensor 7 being measured, (e) $c_g$ being the specific heat of the known respiratory gas, (f) $q_f$ being the heat of evaporation of the liquid anesthetic, and (g) $Q_6$ being the input power of the heating element.

To monitor the flow $M_N$ of the anesthetic, heating element 6 is operated in a controlled manner until the temperatures at inlet temperature sensor 5 and at outlet temperature sensor 8 are equalized, i.e. the difference between temperature $T_5$ and $T_8$ is zero. In this state, the input power of the heating just balances the heat of evaporation of the supplied amount of anesthetic $M_N$. The thermal insulation of housing 1 eliminates interfering influence from the outside. The measurement is independent of the rate of flow $M_g$ of the respiratory gas, since the amount, composition, and temperature thereof are the same in inlet portion 3 and in outlet portion 4.

In operation, heating element 6 heats the respiratory gas amount $M_g$ flowing through inlet portion 3. The temperature $T_7$ establishing at the intermediate temperature sensor 7, is measured. Now it holds for the device that $$M_N \cdot q_f = Q_6 = M_g \cdot c_g \cdot (T_7 - T_5)$$

Temperature sensors 5,7,8 are resistance sensors. They are connected in a bridge circuit, with associated balancing resistances 11, to the inputs of two amplifiers 12, 13. Other known connections for the bridge circuit are shown.

Amplifier 12 supplies heating element 6 to equalize the temperatures measured at inlet temperature sensor 5 and at outlet temperature sensor 8. Ammeter 14 and voltmeter 15 connected in the lines produce through wattmater 16 an indication at 17 corresponding to the anesthetic flow $M_N$.

The signal of wattmeter 16 is at the same time delivered to a computer 18. Amplifier 13 forms a signal from the temperature rise produced by heating element 6 and measured by inlet temperature sensor 5 and intermediate temperature sensor 7, and delivers it to computer 18. In computer 18, the values of respiratory gas flow $M_g$ and anesthetic flow $M_N$ are formed, and the concentration is determined and indicated through indicator 21.

Amplifier 12 in FIG. 2 is a differential amplifier having two inputs. One input is connected for receiving a signal from the outlet temperature sensor 8 and the other input is connected for receiving a signal from the inlet temperature sensor 5. A difference between the inlet and outlet temperatures is amplified and supplied as a power signal to the heater 6. If the inlet and outlet temperatures are equal, the difference is zero so there is no output from amplifier 12 and no power supplied to heater 6. The difference between the inlet and intermediate temperatures at sensors 5 and 6 is measured in the same way using amplifier 13 which has an output 2 connected to computer 18.

If different gas mixtures are used as respiratory gas, the mixture and its specific heat $c_g$ must be known. With known components, (for anesthetic purposes, the components oxygen and laughing gas or oxygen and air are usual), the mixing ratio is determined from the heat conduction. The heat transfer from heating element 6 to the respiratory gas depends on the mixing ratio. A change in temperature of the heating element is measured at intermediate temperature sensor 7. The data are available in storages of computer 18. A selector switch 23 serves the purpose of connecting the respective storage if other components are used. From the signals of ammeter 14 and voltmeter 15, an ohmmeter 19 forms a signal corresponding to the temperature-dependent resistance of heating element 6 and serving in computer 18 as a measure of the temperature of element 6. From the measured values and stored data, computer 18 determines the present mixing ratio, to be indicated at 22, and the flow of respiratory gas, to be indicated at 20.

While a specific embodiment of the invention has been shown and described in detail to illustrate the application of the principles of the invention, it will be understood that the invention may be embodied otherwise without departing from such principles.

What is claimed is:

1. An evaluation device, comprising a housing having a mixing chamber therein, a respiratory gas supply external to said housing, an inlet conduit for respiratory gas having an entrance and being connected to the respiratory gas supply and extending into said housing and into said mixing chamber, an anesthetic supply external to said housing, an anesthetic conduit connected to said anesthetic supply and having a heat exchanger portion in said inlet conduit adjacent said entrance of said inlet conduit, said anesthetic conduit extending through said housing from said heat exchanger portion into said mixing chamber along a path different from said inlet conduit, said inlet conduit being connected into said mixing chamber so as to direct respiratory gas tangentially into said mixing chamber to form a cyclonic pool in said mixing chamber, said anesthetic conduit being connected into said mixing chamber so as to direct anesthetic gas into the formed cyclonic pool in such a manner as to cause evaporation of anesthetic in said mixing chamber, a heater located in said housing adjacent said inlet conduit downstream of said heat exchanger portion for heating said inlet conduit, an inlet temperature sensor in said inlet conduit between said heat exchanger and said heater, an intermediate temperature sensor in said inlet conduit between said heater and said mixing chamber, an outlet conduit extending from said mixing chamber through said housing to the exterior thereof, said housing having means for insulating said inlet, anesthetic and outlet conduits from the exterior, a discharge temperature sensor in said outlet conduit for sensing the temperature of the mixture of evaporated anesthetic and the respiratory gas located in said outlet conduit, and electrical evaluation means connected to each of said inlet temperature sensor, said discharge temperature sensor and said heater for regulating said heater based on temperatures sensed by said inlet and discharge temperature sensors.

2. A device according to claim 1, wherein said electrical evaluation means includes a voltmeter and ammeter connected to said heater for measuring voltage and current supplied to said heater, a first differential amplifier having two inputs connected to said inlet and discharge temperature sensors, respectively, and an output connected to said heater, a wattmeter and an ohmmeter connected to said voltmeter and ammeter, an anesthetic flow indicator connected to said wattmeter, a computer connected to said wattmeter and ohmmeter, a respiratory gas flow indicator, a concentration indicator and a mixing ratio indicator all connected to said computer, and a second differential amplifier having two inputs connected to said inlet and intermediate temperature sensors, respectively, and an output connected to said computer, said first amplifier controlling an amount of power supplied to said heater based on a difference between temperature sensed by said inlet and outlet temperature sensors and for reducing the power to zero when the temperatures sensed by said inlet and outlet temperature sensors is zero, said wattmeter measuring power supplied to said heater which corresponds to a flow of anesthetic into said mixing chamber, said anesthetic flow indicator connected to said wattmeter providing an indication of anesthetic flow, said second amplifier measuring a difference in temperature sensed by said inlet and intermediate temperature sensors which corresponds to a temperature rise caused by said heater, said temperature rise being used in said computer along with outputs of said wattmeter and ohmmeter for calculating values to be applied to said respiratory gas flow indicator, concentration indicator and mixing ratio indicator.

* * * * *